United States Patent [19]

Asselin

[11] 4,419,226

[45] Dec. 6, 1983

[54] RECOVERY OF AROMATIC HYDROCARBONS AND A NON-AROMATIC RAFFINATE STREAM FROM A HYDROCARBON CHARGE STOCK

[75] Inventor: George F. Asselin, Mt. Prospect, Ill.
[73] Assignee: UOP Inc., Des Plaines, Ill.
[21] Appl. No.: 163,446
[22] Filed: Jun. 26, 1980
[51] Int. Cl.$^3$ .............................................. C07C 7/08
[52] U.S. Cl. .................................. 208/325; 208/322; 585/865
[58] Field of Search .................. 208/322, 325; 585/865
[56] References Cited
U.S. PATENT DOCUMENTS 3,556,991  1/1971  Gerhold ............................. 208/325
3,763,037  10/1973  Thompson ......................... 208/325
3,868,310  2/1975  Van Kleef et al. ................. 587/857

Primary Examiner—Earl C. Thomas
Assistant Examiner—Wayne A. Langel

Attorney, Agent, or Firm—James R. Hoatson, Jr.; Robert W. Welch; William H. Page, II

[57] ABSTRACT

A process for the recovery of aromatic hydrocarbons and a non-aromatic raffinate stream from a hydrocarbon charge stock is disclosed. The hydrocarbon charge stock is treated with an aromatics-selective solvent to provide an aromatics-rich solvent stream and a non-aromatic raffinate stream. The aromatics-rich solvent stream is treated in a stripper column at conditions to separate substantially all of the non-aromatic hydrocarbons therefrom. The rich solvent stream is subjected to steam stripping to provide a high purity aromatics stream and an aqueous stream comprising the steam condensate and residual aromatics. This aqueous stream is treated with a minor portion of the non-aromatic raffinate to remove the residual aromatics, and the resulting aqueous stream is utilized to wash the remainder of the raffinate free of solvent. The raffinate stream is recovered substantially free of aromatics.

5 Claims, 1 Drawing Figure

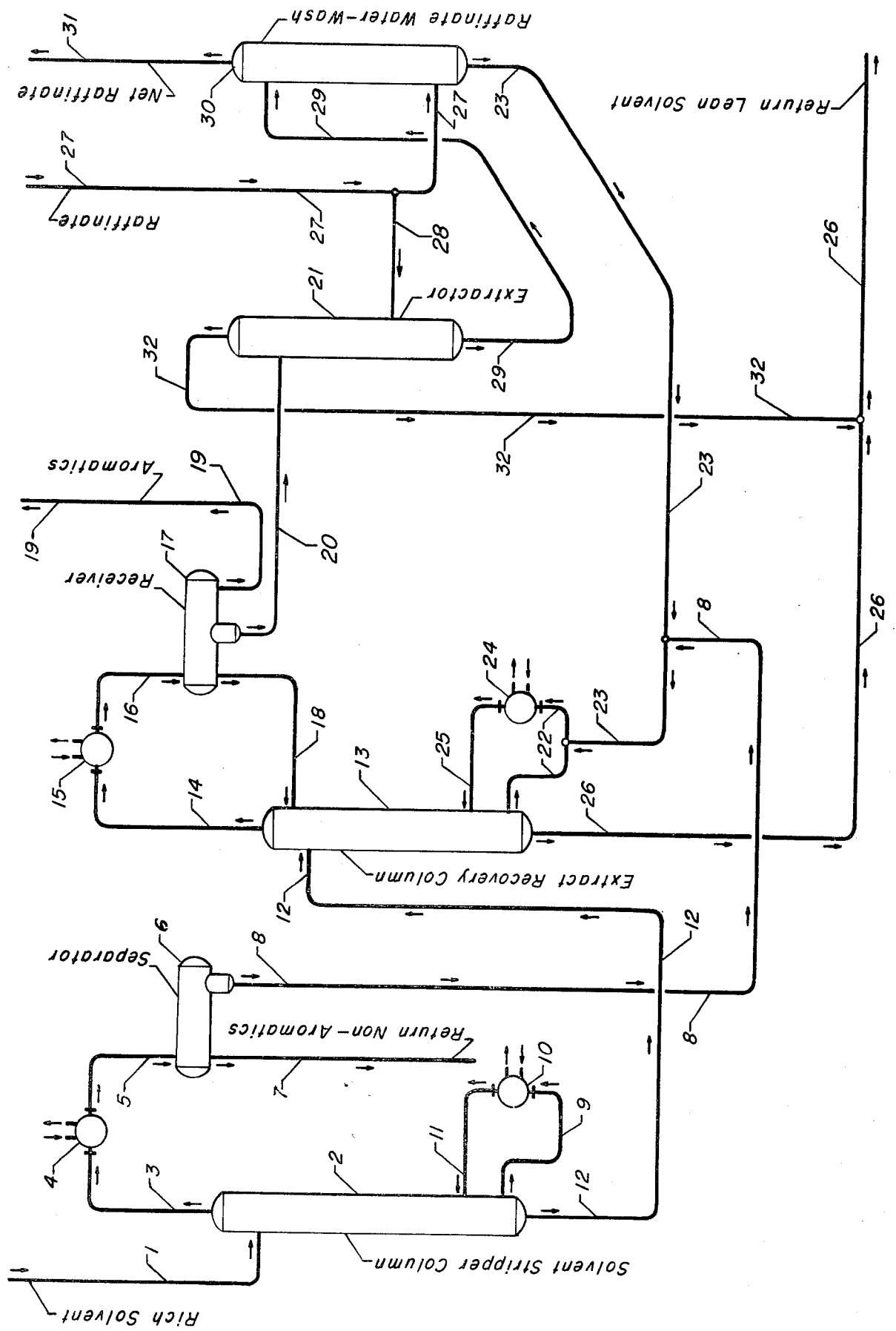

RECOVERY OF AROMATIC HYDROCARBONS AND A NON-AROMATIC RAFFINATE STREAM FROM A HYDROCARBON CHARGE STOCK

The present invention relates to the solvent extraction of aromatic hydrocarbons from a hydrocarbon charge stock. More particularly, this invention relates to the aqueous extraction of solvents from a non-aromatic raffinate produced by the solvent extraction of aromatics from a hydrocarbon charge stock. This invention is more specifically related to an improved process for the aqueous extraction of solvents from a non-aromatic raffinate produced by the solvent extraction of aromatics from a hydrocarbon charge stock, whereby the aqueous extractant is pretreated in contact with a portion of said raffinate.

It is well known in the art that the raffinate which leaves the extraction zone of an aromatic hydrocarbon extraction process contains solvent. The solvent contained in the raffinate stream must be recovered, not only because it may interfere with the subsequent processing or use of the raffinate, but primarily because a continuous loss of solvent is a prohibitive expense to the aromatic extraction process. Recovery of the solvent from the raffinate stream is typically accomplished by distillation of the raffinate or, more preferably, by a secondary solvent extraction process, such as water washing of the raffinate stream.

A typical aromatics-selective solvent utilized in commercial aromatic extraction processes which can be recovered in accordance with the practice of this invention, is commonly referred to as sulfolane (tetrahydrothiophene,1-1 dioxide). Also employed are those sulfolane derivatives corresponding to the structural formula:

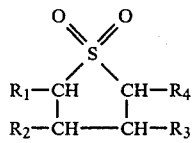

wherein $R_1$, $R_2$, $R_3$ and $R_4$ are independently selected from the group consisting of hydrogen, an alkyl radical containing from about 1 to about 10 carbon atoms, an aralkyl radical having from about 7 to about 12 carbon atoms, and an alkoxy radical having from about 1 to about 8 carbon atoms. Other solvents which may be included within this process are the sulfolenes, such as 2-sulfolene or 3-sulfolene which have the following structures:

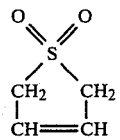

Other typical solvents which have a high selectivity for separating aromatics from non-aromatic hydrocarbons and which may be processed within the scope of the present invention are 2-methylsulfolane, 2,4-dimethylsulfolane, methyl-2-sulfonyl ether, N-aryl-3-sulfonylamine, 2-sulfonyl acetate, diethylene glycol, various polyethylene glycols, dipropylene glycol, various polypropylene glycols, dimethyl-sulfoxide, N-methyl pyrrolidone, etc.

The specifically preferred solvent chemical which is processed within the scope of the present invention is sulfolane having the following structural formula:

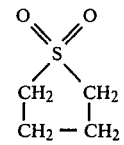

DESCRIPTION OF PRIOR ART

The solvent composition herein contemplated comprises a mixture of water and one or more of the solvents herein noted. A particularly preferred solvent composition comprises water and sulfolane. In extracting aromatic hydrocarbons from the hydrocarbon mixture, it is known that the paraffins are the least soluble followed in increasing order of solubility by naphthenes, olefins, diolefins, acetylenes, sulfur containing hydrocarbons, nitrogen containing hydrocarbons, oxygen containing hydrocarbons and aromatic hydrocarbons. It is the practice to regulate the solubility of the hydrocarbons within the solvent composition by varying the water content thereof. Thus, by adding more water to the solvent, the solubility of all components in the hydrocarbon mixture is decreased but the solubility difference between components (selectivity) is increased. The ned effect is to decrease the number of contacting stages required to achieve a given purity of aromatic extract, or to increase the resulting purity of the aromatic extract when the number of contacting stages is held constant.

The presence of water in the solvent composition provides a further processing benefit in that it introduces a relatively volatile material into the fractionation system wherein the aromatic extract is separated from the rich solvent composition. The water of the solvent composition is vaporized, at least in part, to provide assistance in stripping all traces of non-aromatic hydrocarbons out of the aromatic-rich solvent and to provide assistance in stripping substantially all of the aromatic extract out of the final lean solvent.

It is, therefore, the practice to provide that the solvent composition contain from about 0.1% to about 20% by weight of water. When the solvent composition comprises sulfolane, it is preferable that the solvent composition contain from about 0.1% to about 1.0% of water, while a solvent composition comprising a polyalkylene glycol preferably contains from about 6% to 15% of water.

In an aromatic extraction process typical of the present invention, the hydrocarbon charge stock is treated in an extraction zone which may comprise a tower or column suitably packed with Berl saddles, Raschig rings, and the like, or a column containing suitable trays or baffles, or a rotating disc contactor (RDC). The hydrocarbon charge stock is treated therein in contact with a lean solvent composition at conditions to provide a non-aromatic raffinate and an aromatic-rich solvent composition. The rich solvent composition is recovered from the extraction zone and passed to a separation zone which will generally comprise one or more fractionation columns operated at conditions to remove residual non-aromatic hydrocarbons, and to recover a high purity aromatic extract and a resulting lean solvent composition. The non-aromatics thus removed are normally returned to the extraction zone to provide a non-aromatic hydrocarbon reflux therein. Because the solvents commonly employed in the extraction process are generally unstable at elevated temperatures, it is a common practice to recover the aromatic extract therefrom with the aid of steam stripping—the aromatic extract being subsequently separated from the steam condensate and passed to a fractionation train wherein it is fractionated into its component parts. The steam condensate is typically subsequently utilized to water-wash the first mentioned non-aromatic raffinate for the extraction and recovery of the residual solvent contained therein.

The aromatic extraction process which has been broadly summarized herein above is clearly set forth in U.S. Pat. No. 3,361,664 wherein the solvent composition comprises sulfolane and water. A typical aromatic extraction process wherein the solvent composition comprises polyalkylene glycol and water is disclosed in U.S. Pat. No. 2,773,918. These and other published patent literature clearly set forth typical processing steps and the operating conditions for the aromatic extraction zone which produces a non-aromatic raffinate and an aromatic-rich solvent, and for the subsequent separation zone wherein the rich solvent may be separated to provide a non-aromatic fraction, a high purity aromatic extract, and a final lean solvent.

As previously noted, the non-aromatic raffinate which leaves the extraction zone will contain some solvent. The solvent may be present in the raffinate partly as a soluble constituent in low concentration and partly as an entrained dispersion of free solvent phase due to the turbulence within the extraction zone. Because the typical solvent compositions which are utilized in aromatic extraction are water-soluble, it is the pratice to extract the solvent which is contained in the non-aromatic raffinate stream by contacting this raffinate stream with an aqueous stream in a subsequent extraction means. The extraction of the solvent from the raffinate with water may be undertaken in any suitable liquid-liquid contacting means such as in a tower containing suitable packing such as Berl saddles or Raschig rings, or in a tower containing suitable tray devices, or in a rotating disc contactor (RDC).

The raffinate which then leaves the aqueous extraction zone, or water-wash zone, will be substantially free of the solvent composition. The non-aromatic hydrocarbon raffinate, comprised principally of hexane and heptane, is generally useful as a solvent, although in some cases such use is precluded because of contaminating amounts of aromatics contained therein. One such precluded use is in the solvent extraction of vegetable oils.

The contaminating amounts of aromatics which occur in the non-aromatic raffinate are derived from the aqueous extractant stream utilized in the process of extracting solvent from said raffinate. In the interest of water conservation, the aqueous extractant stream has been provided from the aforementioned stripping steam condensate recovered from the aromatic extract. This stripping steam condensate, from which substantially all of the aromatic extract has been separated, will typically retain from about 300 to about 400 ppm. aromatics which are subject to transfer into the non-aromatic raffinate in the course of extracting the solvent composition therefrom.

It is therefore an object of this invention to present an improved process for the solvent extraction of aromatic hydrocarbons from a hydrocarbon charge stock, and for the recovery of a high purity non-aromatic raffinate. It is a further and more specific object to provide an improved process for the aqueous extraction of solvent from a non-aromatic raffinate produced by the solvent extraction of aromatics from a hydrocarbon charge stock whereby a high purity raffinate is recovered.

It has been determined that the objectives of this invention can be achieved by pretreating the residual aromatics-containing steam condensate recovered from the aromatic extract with only a minor portion of the principal non-aromatic raffinate stream before said condensate is utilized as an aqueous extractant to recover solvent from said principal raffinate stream. In this manner, only a small amount of the raffinate will extract the residual aromatics from the steam condensate—aromatics which would otherwise be extracted by the principal raffinate stream to impair its use, for example, as a high purity solvent.

The present invention embodies a process for the recovery of aromatic hydrocarbons and a raffinate stream substantially free of aromatics from a hydrocarbon charge containing both aromatic and non-aromatic hydrocarbons which comprises: (a) treating said hydrocarbon charge stock in an extraction zone in contact with an aromatics-selective solvent composition at conditions selected to provide a first aromatics-rich solvent stream containing non-aromatic hydrocarbons and a first raffinate stream comprising non-aromatic hydrocarbons and residual solvent; (b) treating said first aromatics-rich solvent stream in a first separation zone at conditions selective to separate substantially all of the non-aromatic hydrocarbons therefrom and to provide a second aromatics-rich solvent stream; (c) treating said second aromatics-rich solvent stream in a second separation zone in contact with stripping steam at conditions selected to provide an aromatics stream comprising aromatics and steam condensate and a lean solvent stream substantially free of aromatic hydrocarbons; (d) treating said aromatics stream of (c) in a third separation zone at conditions selected to provide a high purity aromatics stream and a first aqueous stream containing steam condensate and residual aromatics; (e) returning said lean solvent stream of (c) to said extraction zone of (a); (f) treating said first aqueous stream of (d) containing residual aromatics in a first contacting zone with a minor first portion of said first raffinate stream removed from said extraction zone in (a) at conditions selected to provide a second aqueous stream containing less than 100 ppm aromatic hydrocarbons, and an aromatics containing second raffinate stream; (g) returning said aromatics-containing second raffinate stream of (f) to said extraction zone of (a); (h) treating said second aqueous stream of (f) with a major second portion of said first raffinate stream of (a) in a second contacting zone at conditions selected to provide a third raffinate stream substantially free of aromatic hydrocarbons and solvent-containing aqueous stream; and (i) recovering said third raffinate substantially free of aromatics.

Other objects and embodiments of this invention will become apparent in the following more detailed specification.

The further description of the process of this invention is presented with reference to the attached schematic drawing. The drawing represents one preferred embodiment of this invention and is not intended as an undue limitation on the generally broad scope of the invention as set out in the appended claims.

In illustration of said preferred embodiment, a depentanized catalytic reformate is first rerun to remove the high boiling fraction. The rerun product is then solvent-extracted to produce a nitration grade aromatics fraction consisting of benzene, toluene and xylenes, and a raffinate comprising $C_6$–$C_8$ paraffins and substantially free of aromatics. The rerun feedstock is initially charged to a primary aromatics extraction zone, not shown in the attached drawing, at a rate of about 8730 b.p.s.d., or 1063.6 lb-mols/hr, wherein the feed is contacted with a sulfolane solvent composition. A non-aromatic raffinate stream is produced at a rate of about 4365 b.p.s.d., or 470.8 lb-mols/hr, and an aromatics-rich solvent is recovered at a rate to provide about 1191.9 lb-mols of hydrocarbon extract per hour.

Referring now to the drawing, the rich solvent stream from the primary aromatics extraction zone enters the process of the present invention via line 1. This rich solvent stream furnishes about 1191.9 mols of hydrocarbon extract per hour, and a solvent composition comprising sulfolane and water. The rich solvent stream is continued through line 1 and enters a solvent stripper column 2 at a temperature of about 245° F., and at a pressure of about 5 psig. The solvent stripper column 2 is operated at conditions to separate substantially all of the non-aromatic hydrocarbons from the rich solvent stream charged thereto. Thus, a stripper column overhead stream is recovered through line 3 at a rate of about 659.1 mols/hr, at a temperature of about 265° F., and at a pressure of about 5 psig. This overhead vapor stream is cooled to about 120° F. in a condenser 4, and then passed via line 5 into a phase separator 6 maintained at substantially atmospheric pressure conditions. The vapor condensate is settled in the phase separator 6 to provide an aqueous phase and a hydrocarbon phase. The hydrocarbon phase, comprising principally non-aromatic hydrocarbons, is withdrawn by way of line 7 at a rate of about 592.1 mols/hr and at a temperature of about 120° F. This hydrocarbon stream is typically recycled to the primary aromatics extraction zone, not shown, to provide a non-aromatic reflux therein. The aqueous phase recovered from the phase separator 6 comprises a portion of the water vaporized from the sulfolane-water composition on entering the solvent stripper column 2. This aqueous phase is recovered from the phase separator 6 via line 8 at a rate of about 67 mols/hr, and said aqueous phase is further processed in the manner hereinafter described.

As the rich solvent passes down the solvent stripper column 2, its temperature is increased by the rising hot hydrocarbon and water vapors in a manner sufficient to provide that substantially all non-aromatic hydrocarbons are removed from the rich solvent. An aromatic-rich solvent stream is withdrawn from the bottom of the solvent stripper column 2 by way of line 9 at a temperature of about 300° F. This aromatics-rich solvent stream enters a reboiler 10 wherein the temperature is increased to about 350° F. The resulting hot reboiler vapors and liquid mixture then reenters the bottom of the solvent stripper column 2 via line 11 at about 10 psig.

A resulting stripper bottoms fraction comprising an aromatics-rich solvent leaves the bottom of the solvent stripper column 2 by way of line 12 at a temperature of approximately 350° F. This aromatics-rich solvent stream has been rendered substantially free of non-aromatic hydrocarbons under the conditions at which the solvent stripper column 2 is operated. The aromatics-rich solvent stream is now transferred through line 12 into an extract recovery column 13 at a temperature of about 325° F. and at a pressure of about 300 mm Hg absolute. This aromatics-rich solvent stream contains about 599.8 mols/hr of substantially pure aromatic hydrocarbon, and further comprises a sulfolane solvent composition containing water.

The extract recovery column 13 is operated at conditions to effect the separation of substantially all of the aromatic hydrocarbons from the sulfolane solvent composition. An overhead vapor stream is withdrawn from the extract recovery column 13 by way of line 14 at a temperature of about 180° F. and at a pressure of approximately 300 mm Hg absolute. This hot vapor stream enters condenser 15 and is cooled therein to a temperature of about 100° F. before entering receiver 17 via line 16. The resulting condensate is separated in said receiver 17 into an aromatic hydrocarbon phase and a lower aqueous phase, the latter resulting from the stripping steam utilized in the extract recovery column 13. A first portion of the hydrocarbon phase is withdrawn from the receiver 17 via line 18 and is returned to the extract recovery column 13 as reflux. A second portion of the hydrocarbon phase is withdrawn through line 19 at a rate of about 602.8 mols/hr. This portion of the hydrocarbon phase comprises about 599.8 mols/hr of high purity aromatics and 3 mol/hr of dissolved and entrained water. The aqueous phase which settles out in the receiver 17 contains about 400 ppm residual aromatic hydrocarbons. This aqueous phase, comprising stripping steam condensate, is withdrawn through line 20 at a rate of about 621.9 mols/hr and charged to an aromatics extractor column 21.

Referring back to the extract recovery column 13, as the aromatics-rich solvent passes downwardly therethrough, it is contacted with stripping steam and hot aromatic hydrocarbon vapors whereby substantially all hydrocarbons are stripped from the solvent. A resulting lean solvent leaves the bottom of the extract recovery column 13 via line 22 at a temperature of about 325° F. A combined aqueous stream comprising water, sulfolane, and a small amount of non-aromatic hydrocarbon enters line 22 via line 8 and line 23 from the aforementioned phase separator 6, and via line 23 from a source hereinafter described. The resulting steam and solvent stream passes into reboiler 24 wherein it is heated to about 335° F. The resulting reboiler vapor and liquid mixture leaves the reboiler 24 through line 25 and enters the bottom of the extract recovery column 13.

A net lean solvent leaves the extract recovery column 13 via line 26 at a temperature of about 325° F. and is returned to the aforementioned primary aromatics extraction zone, which is not shown.

The aqueous phase recovered from the receiver 17 and charged to the aromatics extractor column 21 by way of line 20 is contacted therein with a portion of the non-aromatic raffinate stream recovered from the aforementioned primary aromatics extraction zone. The non-aromatic raffinate stream leaves said primary aromatics extraction zone and enters the process of the present invention at a rate of about 470.8 mols/hr via line 27. A small portion of the raffinate stream, about 23.5 mols/hr, is diverted through line 28 and enters the upper portion of the aromatics extractor column 21. Contact is effected in said column at a temperature of about 100° F. and at a pressure of about 60 psig., said column comprising a rotating disc contactor unit or other suitable mixer-settler device. In the aromatics extractor column 21, the non-aromatic component of the raffinate stream charged thereto extracts substantially all of the aromatic component of the aqueous phase charged thereto via line 20. The resulting aqueous phase, containing less than about 100 ppm aromatics, is then withdrawn from the bottom of the aromatics extractor column 21 via line 29 and enters the upper portion of the raffinate water-wash column 30. An overhead stream is recovered from said column 21 via line 32 at a rate of about 23.5 mols/hr and combined with the aforementioned lean solvent stream in line 26 to be returned to the primary aromatics extraction zone.

The raffinate continuing through line 27 to the raffinate water-wash column 30 comprises about 440.6 mols/hr of hydrocarbon and 6.6 mols/hr of sulfolane solvent, and this raffinate enters said column at a temperature of about 100° F., and at a pressure of about 60 psig. The raffinate is water-washed in the water-wash column 30 with about 621.9 mols/hr of 100° F. water entering the top of said column from line 29, said water having been pretreated in the manner heretofore described to contain less than about 100 ppm aromatic hydrocarbons. The raffinate, which is now substantially free of sulfolane, leaves the raffinate water-wash column 30 by way of line 31 at a rate of about 440.18 mols/hr, at a temperature of about 100° F., and at a pressure of about 30 psig. This raffinate stream is sent for further processing at a rate of about 4320 b.p.s.d.

An aqueous stream leaves the raffinate water-wash column 30 at a rate of about 628.97 mols/hr and at a temperature of about 100° F. This stream comprises 621.9 mols/hr of water, 7.0 mols/hr of sulfolane solvent, and 0.07 mols/hr of non-aromatic raffinate. This aqueous stream is transferred via line 23 and combined with the lean solvent in line 22 as heretofore described, and subsequently charged to the extract recovery column 13.

It must be realized that the operating conditions which have been given in the foregoing example are specific to that example and should not be construed as a limitation upon the operation of the present invention. Those skilled in the art may readily ascertain those particular operating conditions which may be required in order to achieve any given separation of non-aromatic raffinate and aromatic extract for any given composition of hydrocarbon charge stock. Broad operating conditions for operation of the primary aromatics extraction zone and for the operation of the rich solvent separation zone may be found in the U.S. patents which have been cited hereinabove or in other well known publications. Those skilled in the art similarly are able to select the operating conditions which may be required in the subsequent aromatic fractionating columns utilized in the typical fractionating train for the aromatic extract.

I claim as my invention:

1. A process for the recovery of aromatic hydrocarbons and a raffinate stream substantially free of aromatics from a hydrocarbon charge containing both aromatic and non-aromatic hydrocarbons which comprises:
   (a) treating said hydrocarbon charge stock in an extraction zone in contact with an aromatics-selective solvent composition at conditions selected to provide a first aromatics-rich solvent stream containing non-aromatic hydrocarbons and a first raffinate stream comprising non-aromatic hydrocarbons and residual solvent;
   (b) treating said first aromatics-rich solvent stream in a first separation zone at conditions selective to separate substantially all of the non-aromatic hydrocarbons therefrom and to provide a second aromatics-rich solvent stream;
   (c) treating said second aromatics-rich solvent stream in a second separation zone in contact with stripping steam at conditions selected to provide an aromatics stream comprising aromatics and steam condensate and a lean solvent stream substantially free of aromatic hydrocarbons;
   (d) treating said aromatics stream of (c) in a third separation zone at conditions selected to provide a high purity aromatics stream and a first aqueous stream containing steam condensate and residual aromatics;
   (e) returning said lean solvent stream of (c) to said extraction zone of (a);
   (f) treating said first aqueous stream of (d) containing residual aromatics in a first contacting zone with a minor first portion of said raffinate stream removed from said extraction zone in (a) at conditions selected to provide a second aqueous stream containing less than 100 ppm aromatic hydrocarbons, and an aromatics containing second raffinate stream;
   (g) returning said aromatics-containing second raffinate stream of (f) to said extraction zone of (a);
   (h) treating said second aqueous stream of (f) with a major second portion of said first raffinate stream of (a) in a second contacting zone at conditions selected to provide a third raffinate stream substantially free of aromatic hydrocarbons and a solvent-containing aqueous stream; and
   (i) recovering said third raffinate stream substantially free of aromatics.

2. The process of claim 1 further characterized in that said aromatics-selective solvent composition comprises a sulfolane type chemical compound of the general formula:

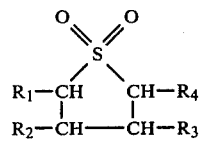

wherein $R_1$, $R_2$, $R_3$ and $R_4$ are independently selected from the group consisting of hydrogen, an alkyl radical containing from about 1 to about 10 carbon atoms, an aralkyl radical having from about 7 to about 12 carbon atoms, and an alkoxy radical having from about 1 to about 8 carbon atoms.

3. The process of claim 1 further characterized in that said aromatics-selective solvent composition is sulfolane of the general formula:

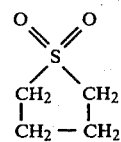

4. The process of claim 1 further characterized in that the solvent-containing aqueous stream of step (h) is returned to the extraction zone of step (a).

5. The process of claim 1 further characterized in that the solvent-containing aqueous stream of step (h) is returned to the second separation zone of step (c).

* * * * *